(12) United States Patent
Claus et al.

(10) Patent No.: US 9,597,041 B2
(45) Date of Patent: Mar. 21, 2017

(54) SEQUENTIAL IMAGE ACQUISITION WITH UPDATING METHOD AND SYSTEM

(75) Inventors: Bernhard Erich Hermann Claus, Niskayuna, NY (US); Kai Erik Thomenius, Clifton Park, NY (US); Frederick Wilson Wheeler, Niskayuna, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 2411 days.

(21) Appl. No.: 11/731,328

(22) Filed: Mar. 30, 2007

(65) Prior Publication Data

US 2008/0242968 A1    Oct. 2, 2008

(51) Int. Cl.
| | |
|---|---|
| A61B 5/00 | (2006.01) |
| A61B 6/03 | (2006.01) |
| A61B 6/00 | (2006.01) |
| G06K 9/20 | (2006.01) |

(52) U.S. Cl.
CPC .............. *A61B 6/032* (2013.01); *A61B 6/469* (2013.01); *G06K 9/20* (2013.01); *G06K 2209/05* (2013.01)

(58) Field of Classification Search
CPC ...................................... A61B 6/032
USPC ........ 600/407, 410, 411, 414, 424–427, 437, 600/439, 443; 382/128, 131, 132; 128/899; 378/9, 16, 20, 37, 151
See application file for complete search history.

(56) References Cited

U.S. PATENT DOCUMENTS

| | | | |
|---|---|---|---|
| 6,480,565 B1* | 11/2002 | Ning | 378/37 |
| 7,123,684 B2* | 10/2006 | Jing et al. | 378/37 |
| 9,165,385 B2 | 10/2015 | Erhard et al. | |
| 2003/0194050 A1* | 10/2003 | Eberhard et al. | 378/37 |
| 2004/0068167 A1* | 4/2004 | Hsieh et al. | 600/407 |
| 2004/0122790 A1* | 6/2004 | Walker et al. | 707/1 |
| 2007/0036402 A1* | 2/2007 | Cahill et al. | 382/128 |
| 2008/0234578 A1 | 9/2008 | Claus | |

FOREIGN PATENT DOCUMENTS

| | | |
|---|---|---|
| CN | 101273919 A | 10/2008 |
| CN | 101273979 A | 10/2008 |
| WO | 2010146483 A1 | 12/2010 |

OTHER PUBLICATIONS

State Intellectual Property Office, P.R. China, Unofficial English Translation of First Office Action issued on Nov. 25, 2010, pages.
Chinese OA, Application 201280063084.2 (issuance #2016070601617340); issued Jul. 11, 2016, w/English Translation; 20 pages.
Unofficial Chinese OA (3rd review), Application 201280063084.2 (issuance #2016070601617340); issued Nov. 1, 2016; 8 pages.

\* cited by examiner

*Primary Examiner* — Rajeev Siripurapu
(74) *Attorney, Agent, or Firm* — Fletcher Yoder, P.C.

(57) ABSTRACT

In accordance with embodiments of the present, a method for acquiring an image is provided. The method comprises acquiring initial image data, identifying one or more regions of interest in at least one of the initial image data or in a first image generated from the initial image data. The method further comprises automatically deriving one or more scan parameters based upon the regions of interest, and acquiring second image data using the scan parameters.

21 Claims, 3 Drawing Sheets

SEQUENTIAL IMAGE ACQUISITION WITH UPDATING METHOD AND SYSTEM

BACKGROUND

The present invention relates generally to the field of medical imaging and more specifically to the evaluation of features of interest in image data acquired by different imaging modalities.

Non-invasive imaging broadly encompasses techniques for generating images of the internal structures or regions of an object or person that are otherwise inaccessible for visual inspection. One of the best known uses of non-invasive imaging is in the medical arts where these techniques are used to generate images of organs and/or bones inside a patient which would otherwise not be visible. One class of medical non-invasive imaging techniques is based on the generation of structural images of internal structures which depict the physical arrangement, composition, or properties of the imaged region. Examples of such modalities include X-ray based techniques, such as CT and tomosynthesis. In these X-ray based techniques, the attenuation of X-rays by the patient is measured at one or more view angles and this information is used to generate two-dimensional images and/or three-dimensional volumes of the imaged region.

Other modalities used to generate structural images may include magnetic resonance imaging (MRI) and/or ultrasound. In MRI, the tissues undergoing imaging are subjected to strong magnetic fields and to radio wave perturbations which produce measurable signals as tissues of the body align and realign themselves based upon their composition. These signals may then be used to reconstruct structural images that reflect the physical arrangement of tissues based on these different gyromagnetic responses. In ultrasound imaging, differential reflections of acoustic waves by internal structures of a patient are used to reconstruct images of the internal anatomy.

Other types of imaging modalities include functional imaging modalities, which may include nuclear medicine, single-photon emission computed tomography (SPECT), and positron emission tomography (PET). These modalities typically detect, either directly or indirectly, photons or gamma rays generated by a radioactive tracer introduced into the patient. Based on the type of metaboland, sugar, or other compound into which the radioactive tracer is incorporated, the radioactive tracer is differentially accumulated in different parts of the patient and measurement of the resulting gamma rays can be used to localize and image the accumulation of the tracer. For example, tumors may disproportionately utilize glucose relative to other tissues such that the tumors may be detected and localized using radioactively tagged deoxyglucose.

Typically, image acquisition events that use different modalities are administered relatively independently of one another. For example, current processes may involve human intervention or interactions between acquisitions of first, second and/or subsequent images (using the same or a different imaging modality) so that initial images can be reviewed and evaluated by a clinician to provide parameters, such as volumes or planes of interest, for subsequent image acquisitions. This tends to prolong the imaging process, resulting in lower efficiency and patient throughput. In addition, such labor intensive processes may result in patient discomfort and increase in the cost of the imaging procedure.

BRIEF DESCRIPTION

The present technique provides a method for processing an image. The method comprises acquiring initial image data to obtain a first image. Based on the initial image data, regions of interest are identified and scan parameters pertaining to those regions (or imaged structures within those regions) are obtained from the first image. Thereafter, a second image or additional images are obtained of the regions of interest based on the scan parameters obtained from the first image. Software and system claims corresponding to this method are also provided.

The present technique further provides a method for acquiring image data from which a first image may be generated, such that at least one of the first image data or the first image comprise one or more regions of interest. The method further provides acquiring second image data based upon one or more scan parameters automatically derived from the one or more regions of interest. Software and system claims corresponding to this method are also provided.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
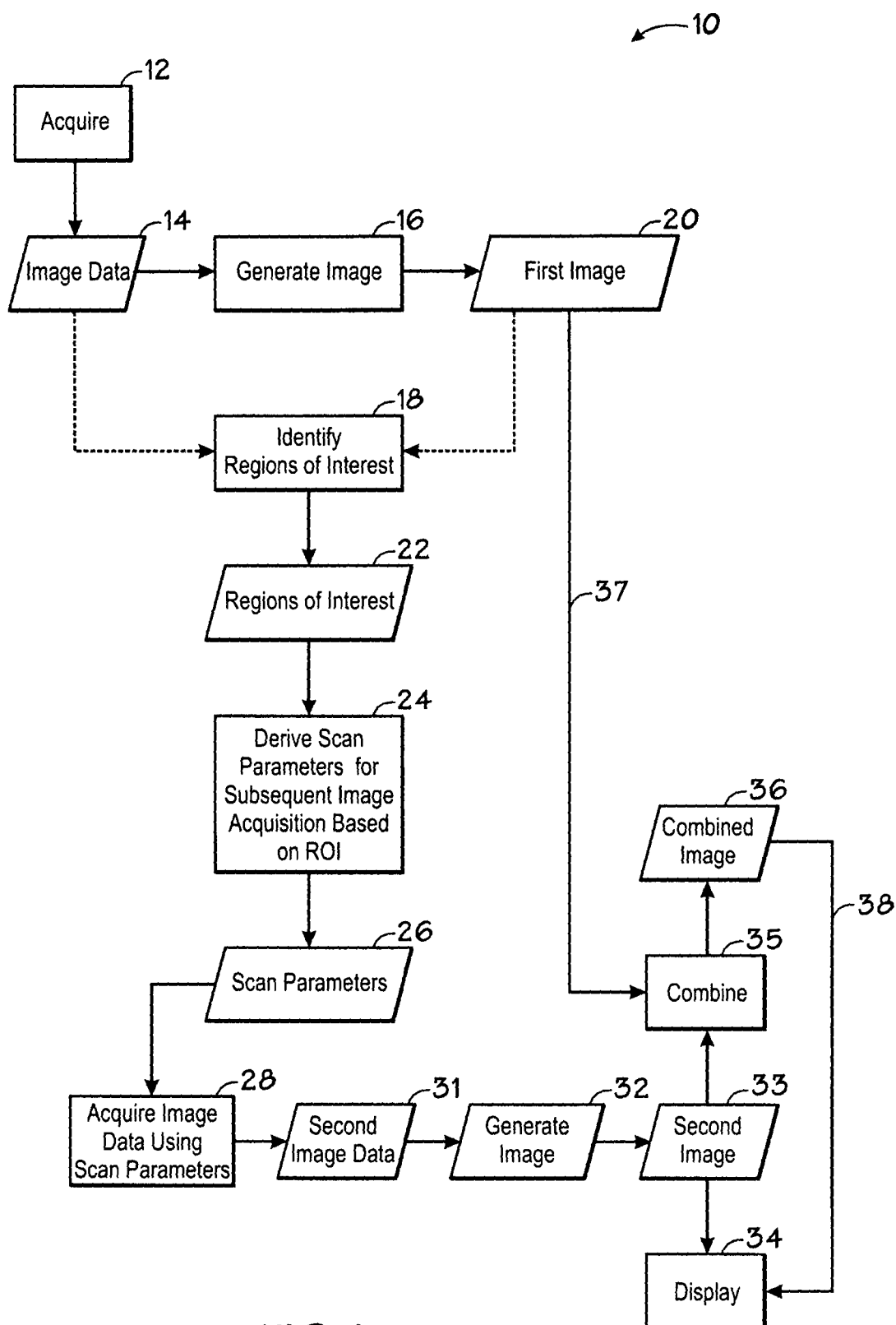
FIG. 1 illustrates a flow chart of a method for processing an image, in accordance with an exemplary embodiment of the present technique.

Turning now to the figures, FIG. 1 illustrates a method 10 for image acquisition and processing, in accordance with an embodiment of the present technique. The method described herein may be implemented by an imaging system having a single imaging modality or one having multiple imaging modalities. Alternatively, the method may be implemented in separate imaging systems that share a common coordinate system for an imaged volume, or where a known mapping between the coordinate systems exists. The method includes using image or scan parameters obtained from an initial image acquired by one imaging modality for use in acquisitions of subsequent images performed by the same or a second imaging modality. The method provides an automated process whereby the initial image provides pertinent information for subsequent image acquisitions.

The method summarized in FIG. 1 begins at step 12 where data of an initial image is acquired. As discussed further below, data acquisition may be based upon any suitable imaging modality, typically selected in accordance with the particular anatomy and/or lesion or pathology to be imaged and the analysis to be performed. By way of example, those skilled in the art will recognize that the underlying physical processes by which certain imaging modalities function render them more suitable for imaging certain types of tissues or materials or physiological processes, such as soft tissues as opposed to bone or other more dense tissue or objects. Moreover, a scan or examination performed by the modality may be executed based upon particular settings or scan parameters, also typically dictated by the physics of the system, to provide higher or lower contrast images, sensitivity or insensitivity to specific tissues or components, and so forth. Finally, the image acquisition may be performed on tissue that has been treated with contrast agents or other markers designed for use with the imaging modality to target or highlight particular features or areas of interest. In a CT system, for example, the image data acquisition of step 12 is typically initiated by an operator interfacing with the system via the operator workstation 70 (see FIG. 2). Readout electronics detect signals generated by virtue of the impact radiation on the scanner detector, and the system processes these signals to produce useful image data.

Returning now to FIG. 1, initial image data 14 is provided as an output from the image acquisition process of step 12. From the image data 14 an image 20 is generated (block 16), typically by using a reconstruction processing step. Such reconstruction processing may utilize computer implemented codes and/or algorithms used, for example, to convert image data in frequency space into an image in real coordinate space. The image generation process of step 16 provides a first image 20. The first image 20 may be displayed or used as an input to other processes. In general, an initially formed image 20 may be used by a clinician to, for example, identify and analyze features of interest as part of an initial diagnostic procedure.

In addition to being provided for image generation, as performed in block 16, the image data 14 and/or the initial image 20 may be processed and/or analyzed (block 18) to identify regions of interest 22 within the image data 14 and/or the image 20. In one implementation, the identification step 18 may be automatically or semi-automatically performed, with no or limited review by a clinician. The identification step 18 may be automated and may include utilizing computer aided detection or diagnosis (CAD) evaluation of the initial image 20 and/or image data 14 to detect, label and classify, for example, suspicious regions contained within the initial image 20 and/or image data 14. Accordingly, at step 18, one or more CAD algorithms may be executed to implement the act of identifying the regions of interest 22. The CAD algorithm will typically be selected in accordance with the imaging modality and with the particular data type and anatomy represented in the image. As an initial processing step, the imaged anatomy may be automatically identified and/or accurately located within the image and the CAD algorithm and/or specific parameter settings may be selected based on the identified anatomy. Parameter settings may include, but are not limited to, location of features or regions of interest, view angles, image resolution, dose levels of X-rays or other forms of radiation used in nuclear medicine, beam energy level settings of X-ray tubes, film parameters, ultrasound transducer power level settings, scan duration, MRI pulse sequences, projection angles and so forth. In other embodiments, parameter settings may be selected manually by a user according to the identified anatomy and/or other operational needs. In one embodiment, regions of interest in the displayed image are selected manually by a user, and the corresponding scanning parameters are automatically derived.

The CAD analysis may identify various features of interest 22, including their location, disease states, lesions, or any other anatomical or physiological features of interest. In one embodiment, based upon the analysis, one or more target regions are selected as regions designated for further imaging by the same or other imaging modalities. By way of example, subsequent imaging of the target region 22 selected at step 18 may provide for greater spatial resolution (e.g. zoom-in) of a potential lesion. In one embodiment, projections of the target region at additional view angles are acquired, e.g., in order to achieve improved 3D characterization of the lesion located in the target region, when reconstructed using image data from the initial view angles and the additional view angles. In one implementation, the target region 22 is selected automatically based upon the output of a CAD analysis. Where, for example, the CAD analysis indicates that acquisition of additional data and subsequent processing may reveal additional details in an image, a target region 22 corresponding to the location of such details will be selected at step 18 in such an implementation.

Accordingly, block 18 provides one or more regions of interest 22 identified from the image data 14 and/or the first image 20. In the depicted embodiment, scan parameters 26 are derived (block 24) based upon the one or more identified regions of interest 22, and/or on characteristics of structures contained within that region of interest. For example, in one embodiment, the act 24 of deriving the scan parameters 26 may include, for example, classification and/or location of anatomy based on input projection and/or reconstructed 3-D data, as provided by, for example, tomosynthesis. Likewise, in other implementations, the act 24 of deriving may include localization and/or identification of other anatomical structures of diagnostic or contextual interest. These may include structural markers, such as BB's or other objects placed on or in the patient to identify a location where more thorough scanning is desired. Further, the act 24 of deriving scan parameters 26 may include identifying certain types of tissue and their extent in the image plane so that subsequent images acquired may focus only on those regions. For example, in tomosynthesis mammogram imaging, initial images 20 are acquired in three-dimensions so that, for example, the skin-line of the imaged breast may be found. Once the skin line is obtained, relevant scan parameters 26 may be extracted from the tomosynthesis image data so that subsequent images acquired, for example, by an ultrasound modality may focus only on the region bounded by the skin-line, thereby minimizing the ultrasound scan time and the overall imaging procedure time. In another exemplary embodiment of the present technique, a tomosynthesis dataset consisting of few (two or more) projections of a chest region of a patient is acquired. A CAD processing step may analyze each of the projection images for the suspected presence of cancerous lesions. By suitably combining the information from the two or more projection images, the 3D locations of suspected lesions can be identified, and additional projections of these regions can be acquired such as to increase the confidence in the CAD result, or in order to gain more information to characterize the lesion, or to perform a high-resolution reconstruction of the region containing the suspected lesion. Scan parameters that are chosen based on the first set of projection images may include view angles, collimator settings so as to, for example, restrict the field of view to the regions of interest, thereby reducing dose to the patient etc. In one embodiment, the region of interest containing a suspected lung nodule may be imaged with a different X-ray energy setting (different kVp). The additional information may now be used in order to determine whether the nodule is calcified, thereby giving information about the malignancy of the nodule. In subsequent analysis or reconstruction steps, all projection images acquired from the first set as well as those acquired from all following acquisition steps may be used in combination.

In some embodiments, the act of deriving (block 24) scan parameters 26 may also include incorporating image data from previous scans of the patient for use in anatomical change detection, i.e., changes in the tissue arising between the preceding and current examination. In the illustrated embodiment, the act of deriving may also include a change detection routine using CAD in which anatomical and/or physiological changes of a patient occurring between subsequent exams are detected. Such change detection procedures may also be performed manually by a clinician who may visually compare images obtained from subsequent exams. In other embodiments, change detection may be done such that imaged anatomy is compared to an "atlas" which represents a "nominal anatomy." Other embodiments may include difference detection based on asymmetry such as implemented, for example, in breast imaging whereby mammograms are usually displayed side by side for detecting asymmetric differences between right and left breasts. This technique can further be employed to determine whether certain regions require more thorough scanning by the same or different imaging modalities. While in one embodiment the process of obtaining scan parameters 26 from the initial image 20 and/or image data 14 is automated, in other embodiments this process may be done with the assistance of an operator or a clinician.

The scan parameters 26, as derived at step 24, may configure or control an additional scan (block 28) in which a second set of image data 31 may be obtained by the same imaging modality used to acquire the initial image or by a different imaging modality. Such scan parameters 26 may include location of features or regions of interest, view angles, image resolution, dose levels of X-rays or other forms of radiation used in nuclear medicine, beam energy level settings of X-ray tubes, film parameters, ultrasound transducer power level settings, scan duration, MRI pulse sequences, projection angles and so forth.

In one embodiment, the process of acquiring the second set of image data 31 is automated, requiring no human intervention. In other embodiments, a clinician/operator may assist and/or intervene in acquiring and/or analyzing the second image data 31. For example, in breast imaging, initial images 20 may be formed from standard mammogram or tomosynthesis data sets consisting of X-ray projections. Accordingly, subsequent data sets 31 may be acquired by another X-ray based modality, providing additional X-ray projections or radiographs, or by a non-X-ray based imaging modality, such as ultrasound or MRI. The subsequently acquired image data 31 may be processed (block 32) to generate one or more second additional images 33.

Hence, the scan parameters 26 derived based upon a first image 20 or image data 14 provide suitable information such that the subsequently generated images 33 can be optimally generated. In other words, the acquisition of the second image 33 is customized based upon attributes or regions identified in the first image 20 or image data 14. Thus, the second image 33 may, for example, focus on certain parts of tissue and/or skeletal structures generally identified in the first image 20 as having suspicious or irregular features, i.e., regions of interest 22. For example, the second image 33 may be acquired in a manner that enhances the spatial resolution, and/or contrast of those suspicious regions of interest 22. In an exemplary embodiment, where ultrasound is employed for acquiring the second image 33, analysis of the initial image 20 may determine to what extent particular ultrasound modes should be used in acquiring the second image 33. Exemplary ultrasound modes may include Doppler ultrasound, strain imaging, compound ultrasound imaging, imaging angles (for steered ultrasound) and so forth.

As depicted in the illustrated embodiment, the second image 33 can be displayed (block 34) on a display device, such as a monitor, and presented to a clinician. Further, in some embodiments the second image 33 and/or second image data 31 can be evaluated in a manner similar to that described above with respect to the first image 20 and/or first image data 14 to identify additional features or regions of interest and/or to derive parameter settings for additional acquisitions. That is, the second image 33 and/or second image data 31 can undergo an automated analysis to identify regions of interest from which additional scan parameters are obtained. The analysis step may also be based on the combined data from the first and the second acquisition. Accordingly, this information can be utilized in subsequent image acquisitions to generate additional images having desirable features identified in the first and second images and/or their respective image data.

In one embodiment, the second image 33 can be combined (block 35) with the first image 20 to generate a combined image 36. The combined image 36 may be displayed (block 34) as discussed above. The act 35 of combining the first and second images 20, 33 may include registering the first and second images 20, 33 based on, for example, landmarks identified in the images. The act of combining the images may also include a single combined reconstruction step based on the combined image data 14, 33 from the first and the second acquisition. Registration may also be based on fiducial markers or on positional/directional information provided by a navigation system e.g., a position/orientation sensor embedded in an ultrasound probe. Registration may also be based on hybrid approaches which combine the aforementioned fiducial markers etc., with anatomical landmarks.

Further, in combining the first and second images 20, 33, multi-modality CAD may be employed in combining information from multiple modalities, thereby simultaneously leveraging the data for diagnostic purposes. For example, detection and/or classification of disease and/or anatomical structures, as well as, functional studies of various physiological processes may be leveraged or enhanced by taking advantage of multi-modal information present in the combination of first and second images 20, 33 and/or in the combined image 36.

In addition, the act 35 of combining the first and second images 20, 33 may include displaying the first and second images 20, 33 side by side. Alternatively, the images 20, 33 may be displayed one at a time such that, for example, CAD analysis from the two images may be utilized in indicating specific regions of interest in each image. It should be borne in mind that the above combination of images can be implemented with any number of acquired images, that is two or more images, and the combination of two images is described merely as an example to simplify discussion.

In one exemplary embodiment of the method 10, evaluation of the images 20, 33 and/or the image data 14, 31 and the identification of the regions of interest 22 are fully automated as is the extraction of the scan parameters 26. Further, in such an implementation, subsequent images may be acquired automatically as well and may in turn facilitate additional automated image acquisition and/or analysis.

Figure 2:
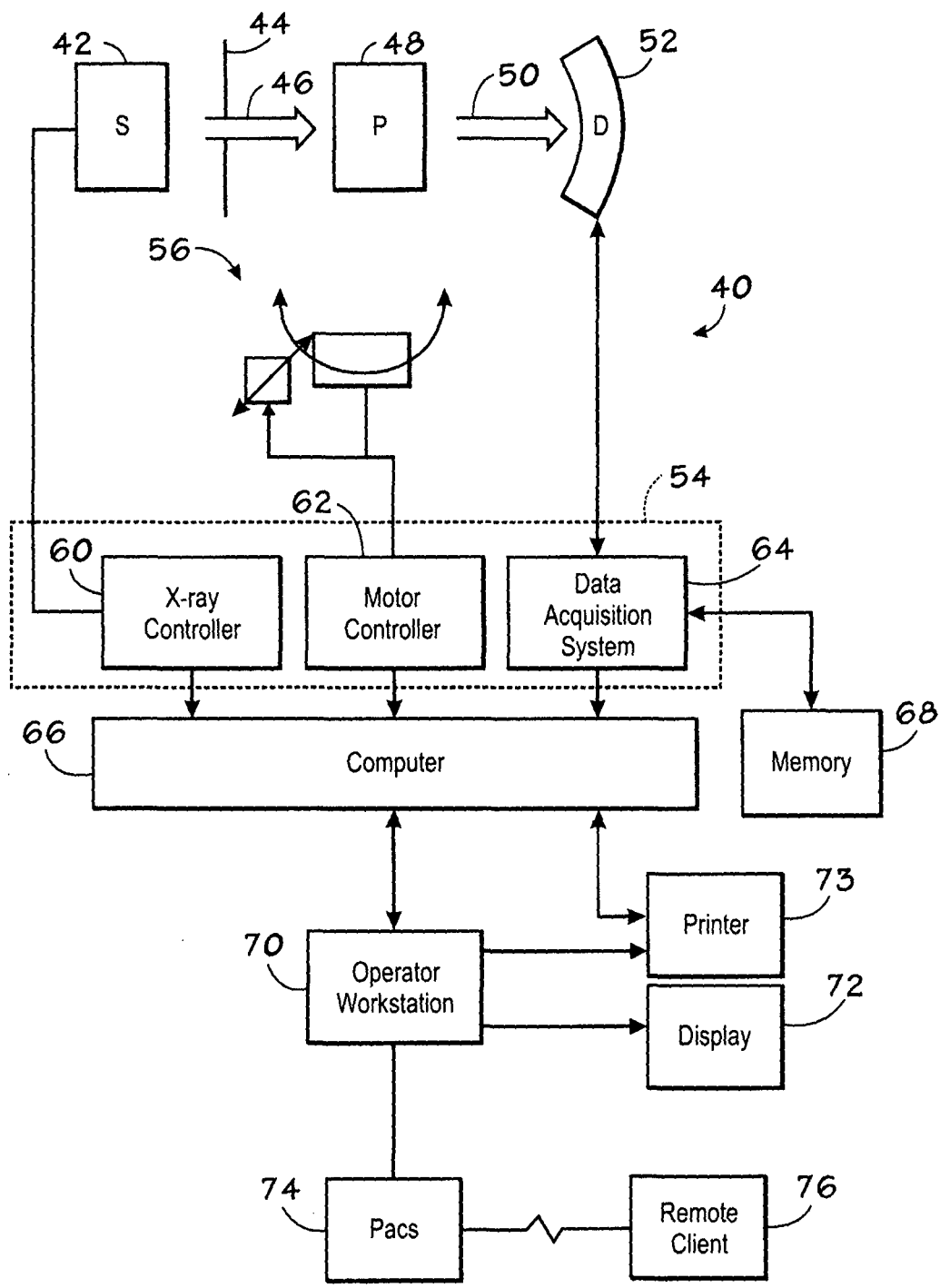
FIG. 2 illustrates a tomosynthesis imaging system, in accordance with an exemplary embodiment of the present technique.

The method 10 described above with regard to FIG. 1 may be implemented in an imaging system 40 shown in FIG. 2. In the illustrated embodiment, system 40 is a tomosynthesis system designed both to acquire original image data, and to process the image data for display and analysis in accordance with the present technique. In the embodiment illustrated in FIG. 2, imaging system 40 includes a source of X-ray radiation 42 positioned adjacent to a moveable and configurable collimator 44 such as may be used for shaping or directing the beam of X-rays emitted by the source 42. In one exemplary embodiment, the source of X-ray radiation source 42 is typically an X-ray tube.

Collimator 44 permits a stream of radiation 46 to pass into a region in which a subject, such as a human patient 48 is positioned. A portion of the radiation 50 passes through or around the subject and impacts a detector array, represented generally at reference numeral 52. Detector elements of the array produce electrical signals that represent the intensity of the incident X-ray beam. These signals are acquired and processed to reconstruct an image of the features within the subject.

Source 42 is controlled by a system controller 54 which furnishes both power and control signals for tomosynthesis examination sequences. Moreover, detector 52 is coupled to the system controller 54, which commands acquisition of the signals generated in the detector 52. The system controller 54 may also execute various signal processing and filtration functions, such as for initial adjustment of dynamic ranges, interleaving of digital image data, and so forth. In general, system controller 54 commands operation of the imaging system to execute examination protocols and to process acquired data. In the present context, system controller 54 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 2, system controller 54 is coupled to a movement subsystem 56. The movement subsystem 56 provides positioning information for one or more of source, collimator (position and aperture shape/size), detector, and a patient support, if present. The movement subsystem 56 enables the X-ray source 42, collimator 44 and the detector 52 to be moved relative to the patient 48. It should be noted that the movement subsystem 56 may include a gantry or C-arm, and the source, collimator and detector may be moved rotationally. Thus, the system controller 54 may be utilized to operate the gantry or C-arm. In some embodiments, the movement subsystem 56 may also linearly displace or translate the source 42 or a support upon which the patient rests. Thus, the source and patient may also be linearly displaced relative to one another in some embodiments. Other trajectories of source, collimator, and detector are also possible. In some embodiments, acquisition of different view angles may be achieved by using individually addressable source points.

Additionally, as will be appreciated by those skilled in the art, the source of radiation may be controlled by an X-ray controller 60 disposed within the system controller 54. Particularly, the X-ray controller 60 is configured to provide power and timing signals to the X-ray source 42. A motor controller 62 may be utilized to control the movement of the movement subsystem 56.

Further, the system controller 54 is also illustrated as including a data acquisition system 64. In this exemplary embodiment, the detector 52 is coupled to the system controller 54, and more particularly to the data acquisition system 64. The data acquisition system 64 receives data collected by readout electronics of the detector 52. The data acquisition system 64 typically receives sampled analog signals from the detector 52 and converts the data to digital signals for subsequent processing by a computer 66.

The computer 66 is typically coupled to the system controller 54. The data collected by the data acquisition system 64 may be transmitted to the computer 66 and moreover, to a memory 68. It should be understood that any type of memory to store a large amount of data may be utilized by such an exemplary system 40. The computer system 66 is configured to implement CAD algorithms required in the identification and classification of regions of interests, in accordance with the method 10 described above. Also the computer 66 is configured to receive commands and scanning parameters from an operator via an operator workstation 70, typically equipped with a keyboard and other input devices. An operator may control the system 40 via the input devices. Thus, the operator may observe the reconstructed image and other data relevant to the system from computer 66, initiate imaging, and so forth. Alternatively, as described above, the computer 66 may receive automatically or semi-automatically generated scan parameters 26 or commands generated in response to a prior image acquisition by the system 40.

A display 72 coupled to the operator workstation 70 may be utilized to observe the reconstructed image and to control imaging. Additionally, the scanned image may also be printed on to a printer 73 which may be coupled to the computer 66 and the operator workstation 70. Further, the operator workstation 70 may also be coupled to a picture archiving and communications system (PACS) 74. It should be noted that PACS 74 may be coupled to a remote system 76, radiology department information system (RIS), hospital information system (HIS) or to an internal or external network, so that others at different locations may gain access to the image and to the image data.

It should be further noted that the computer 66 and operator workstation 76 may be coupled to other output devices which may include standard or special purpose computer monitors and associated processing circuitry. One or more operator workstations 70 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

System 40 is an example of a single imaging modality employed to implement method 10 descried in FIG. 1. In an exemplary implementation of the method, a tomosynthesis scan of the patient 48 is first performed in which anatomical parts are irradiated by X-rays emanating from X-ray source 42. Such anatomical regions may include the patient's breast, lungs, spine and so forth, as facilitated by the movement subsystem 56. The X-rays transmitted through the patient 48 are detected by detector 52, which provides electrical signals data to the system controller 54 representative of the projected X-rays. Upon the digitization of those signals the data is provided to computer 66 which, in one embodiment, performs a reconstruction of an image and implements a CAD algorithm to identify suspicious regions, and/or classify different anatomical structures.

Hence, in such an X-ray imaging procedure initial images may be taken to identify regions of interest, as performed by the computer 66. In so doing, desired scan parameters may be obtained for use in subsequent image acquisitions and processing. For example, identification of a suspicious region, via the CAD analysis, may automatically trigger additional X-ray acquisitions by the imaging system 40 of the region of interest at additional view angles, at a higher resolution or using different resolution or exposure parameters to enhance subsequent image information, such as resolution, shape and size information and other related characteristics. For example, based on the scan parameters obtained in the first image, computer 66 may direct system controller 54, particularly, X-ray controller 60 and motor controller 62, to position the X-ray source, collimators, detectors and patient 48 in manner that directs and collimates the X-ray beam from the desired view angle towards the regions of interest. Hence, additional projection images may be acquired to provide improved and more detailed images of the regions of interest. Once images are acquired and formed, the images can be stored in memory 68 for future retrieval or presented, via display 72, to a clinician for evaluation and diagnostic purposes. Additional acquisitions may be requested for "hard" regions, e.g., dense regions in, for example, the breast region, where initial acquisitions do not penetrate enough to get acceptable image quality. Such regions may be identified using a CAD type system (e.g., by determining regions that cannot be classified as "normal" or "benign" with high confidence), or a clinician may designate the "hard" regions, or regions containing suspicious lesions.

Figure 3:
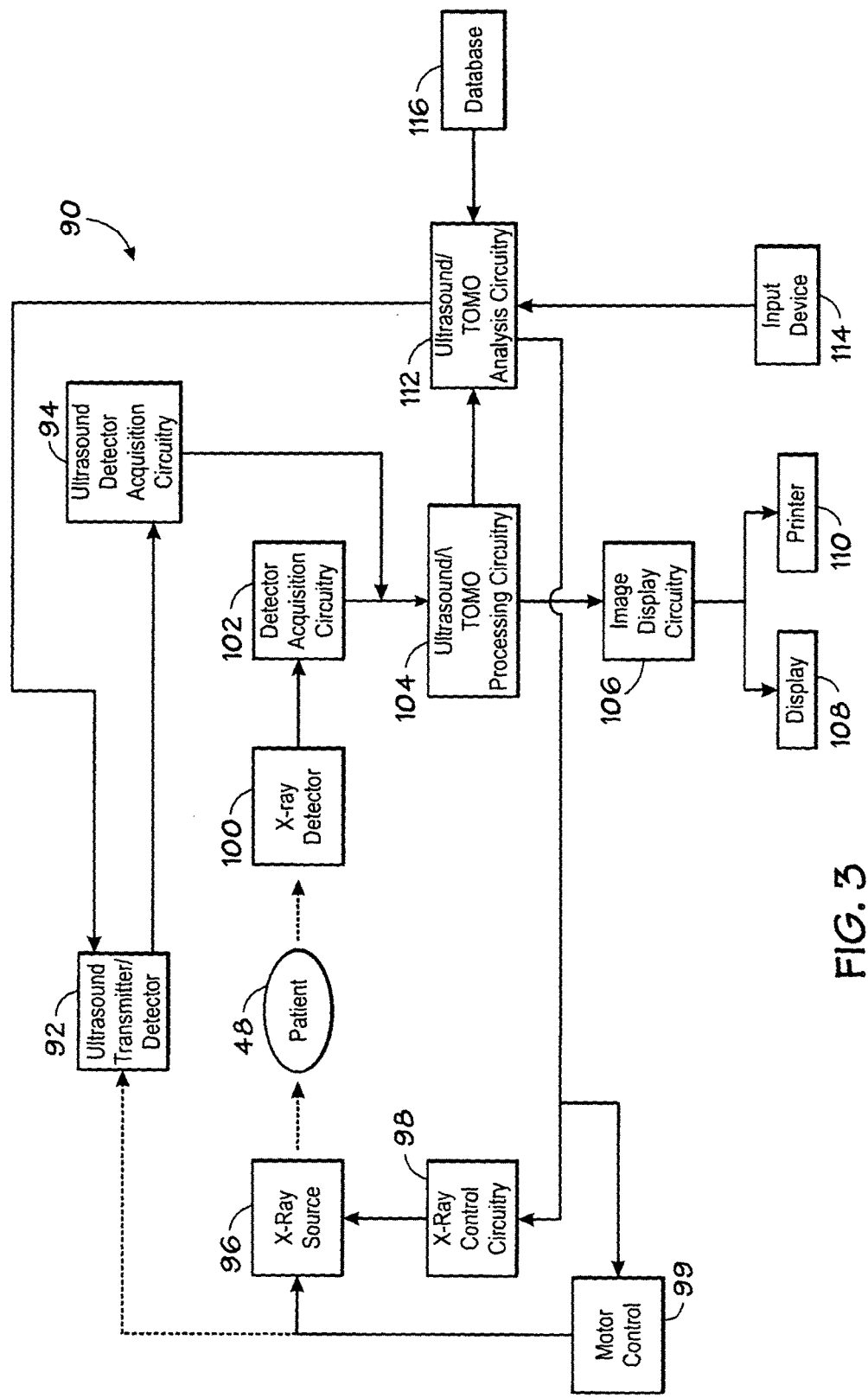
FIG. 3 illustrates a combined imaging system, in accordance with an exemplary embodiment of the present technique.

Referring now to FIG. 3, an exemplary combined ultrasound and tomosynthesis (US/TOMO) imaging system 90 is depicted as an exemplary system used in implementing the method 10 of FIG. 1. The exemplary US/TOMO image analysis system 90 includes tomosynthesis scanning components, including an X-ray source 96 configured to emit X-rays through an imaging volume containing the patient 44 and X-ray control circuitry 98 configured to control the operation of the X-ray source 96 via timing and control signals. In addition, the included X-ray scanning components include an X-ray detector 100 configured to detect X-rays emitted by the source 96 after attenuation by the patient 48. As will be appreciated by those of ordinary skill in the art, the source 96 and X-ray detector 100 may be structurally associated in a number of ways. For example, the source 96 and X-ray detector 100 may both be mounted on a rotatable gantry or C-arm. The X-ray source 96 is further coupled to an X-ray controller 98 configured to provide power and timing signals to the X-ray source 96.

In the depicted system, signals are acquired from the X-ray detector 100 by the detector acquisition circuitry 102. The detector acquisition circuitry 102 is configured to provide any conversion (such as analog to digital conversion) or processing (such as image normalization, gain correction, artifact correction, and so forth) typically performed to facilitate the generation of suitable images. Furthermore, the detector acquisition circuitry 102 may be configured to acquire diagnostic quality images, such as by utilizing prospective or retrospective gating techniques. While utilizing such a technique, it may be beneficial to employ, for example, registration in the projection domain and/or in the reconstructed image domain so as to account for respiratory phases and/or movement of anatomical structures. In such embodiments, higher quality images are acquired than in embodiments in which the patient 44 breathes and no compensation or correction is made for the respiratory motion.

The exemplary US/TOMO image analysis system 90 also includes ultrasound scanning components, including an ultrasound transducer 92. In addition, the exemplary US/TOMO image analysis system 90 includes ultrasound acquisition circuitry 94 configured to acquire signals from the ultrasound transducer 92. The ultrasound acquisition circuitry 94 is configured to provide any conversion or processing typically performed to facilitate the generation of suitable ultrasound images. In one embodiment, depicted by a dotted line, the motor control 99 is also configured to move or otherwise position the ultrasound transducer 92 in response to scan parameters provided to the motor control 99, such as from US/TOMO analysis circuitry 112, as described below.

In the depicted embodiment, the acquired ultrasound and/or tomosynthesis signals are provided to US/TOMO image processing circuitry 104. For simplicity, the US/TOMO image processing circuitry 104 is depicted as a single component though, as will be appreciated by those of ordinary skill in the art, this circuitry may actually be implemented as discrete or distinct circuitries for each imaging modality. Conversely, the provided circuitry may be configured to process both the ultrasound and the tomosynthesis image signals and to generate respective ultrasound and tomosynthesis images and/or volumes therefrom. The generated ultrasound and tomosynthesis images and/or volumes may be provided to image display circuitry 106 for viewing on a display 108 or print out from a printer 110.

In addition, in the depicted embodiment, the ultrasound and tomosynthesis images are provided to US/TOMO analysis circuitry 112. The US/TOMO analysis circuitry 112 analyzes the ultrasound and/or tomosynthesis images and/or volumes in accordance with analysis routines, such as computer executable routines including CAD that may be run on general purpose or dedicated circuitry. In particular, in one embodiment, the US/TOMO analysis circuitry 112 is configured to assign probabilities as to the presence of malignancy, and/or classify regions in the tissue for determining confidence levels associated with existing pathologies. Accordingly, having the benefit of a second round of data acquisitions, classification of potential pathologies will be improved, thereby increasing confidence in the diagnosis. The circuitry 112 may further be adapted to measure, for example, malignancy characteristics of a lesion that are visually or automatically identifiable in the respective ultrasound and tomosynthesis images or in the combined US/TOMO image data. The US/TOMO analysis circuitry 112 may identify and/or measure malignancy characteristics such as shape, vascular properties, calcification, and/or solidity with regard to a lesion observed in the TOMO image data.

Thus, in implementing the method 10 of FIG. 1, US/TOMO analysis circuitry 112 may implement a CAD analysis on a first image acquired by the X-ray detector 100 to identify regions of interest. Thereafter, the US/TOMO analysis circuitry 112 acquires scan parameters from those regions of interest so as to automatically prompt the ultrasound transducer/detector 92 to acquire a second image of the regions of interest or to acquire images having the desired resolution or image quality. Accordingly, this may include performing an ultrasound scan of a whole volume so as to, for example, confirm "negative" classifications obtained in the images acquired by the X-ray system. Further, ultrasound image data acquired in the second image of the regions of interest can be used to supplement CAD output obtained from the X-ray data sets, e.g., classifying a detected feature in the tomosynthesis X-ray data set as a cyst or as a mass. If further evaluations are desired, additional ultrasound data sets may be acquired using, for example, strain or Doppler imaging. In addition, it may be desirable to employ an ultrasound scanning method known as "compounding" in which a region of interest is multiply scanned by the ultrasound from different view angles. Utilizing such a technique can significantly improve the overall image quality of the ultrasound scan and further increase confidence in classification of anatomical structures in the regions of interest. Further, in some embodiments, information or imaging data from more than one modality (such as from tomosynthesis or CT and ultrasound) may be used to further improve image quality. Examples of some exemplary techniques using image data from multiple modalities are discussed in the U.S. Patent Application Serial No. 2008/0234578, entitled "Multi-modality Mammography Reconstruction Method and System" and filed on Mar. 19, 2007 to Bernhard Claus, herein incorporated by reference in its entirety.

The US/TOMO analysis circuitry 112 is also connected to motor control 99 for positioning X-ray source 96 in subsequent X-ray acquisitions. In another exemplary embodiment, after the CAD analysis on a first image acquired by the X-ray detector 100 identifies regions of interest, additional X-ray images of these regions of interest may be acquired at additional view angles. In this way, the reconstructed image quality using both sets of images can be improved, thereby leading to better characterization of the imaged region, and higher confidence in the CAD result.

Furthermore, the US/TOMO analysis circuitry 112 may automatically detect, for example, lesions for which malignancy characteristics can be measured, such as by using threshold criteria or other techniques known in the art for segmenting regions of interest. Alternatively, a clinician or other viewer may manually detect the lesions or other regions of interest in either or both of the ultrasound or tomosynthesis images and/or volumes (such as in images viewed on the display 108). In accordance with the present technique, based on an initial scan a clinician may manually identify ROI by, for example, visually inspecting initial images. Similarly, based on the initial scan the clinician may also manually select scan parameters to be used by the system 40 in subsequent imaging scans. The clinician may then, via input device 114 (such as a keyboard and/or mouse), identify the lesions for analysis by the US/TOMO analysis circuitry 112. In addition, to facilitate analysis either the US/TOMO analysis circuitry 112 or image processing circuitry 104 may register the ultrasound or tomosynthesis images such that respective regions in each image that correspond to one another are aligned. In this manner, a region identified in an image of one modality may be properly identified in images generated by the other modality as well. For example, deformable registration routines (or other registration routines which account for patient motion) may be executed by the US/TOMO image processing circuitry 104 or by the US/TOMO analysis circuitry 112 to properly rotate, translate, and/or deform the respective images to achieve the desired correspondence of regions. Such deformable registration may be desirable where the ultrasound and tomosynthesis data is acquired serially or where the data acquisition period for one of the modalities, such as ultrasound, is longer than for the other modality, such as tomosynthesis. As will be appreciated by those of ordinary skill in the art, other registration techniques, such as rigid registration techniques, that achieve the desired degree of registration or correspondence can also be used in conjunction with the present technique.

While the input device 114 may be used to allow a clinician to identify regions of interest in the ultrasound or tomosynthesis images, the input device 114 may also be used to provide operator inputs to the US/TOMO image analysis circuitry 112. These inputs may include configuration information or other inputs that may select the analysis routine to be executed or that may affect the operation of such an analysis routine, such as by specifying variables or factors taken into account by the analysis routines. Furthermore, inputs may be provided to the US/TOMO image analysis circuitry 112 from a database 116 or other source of medical history that may contain information or factors incorporated into the analysis of the ultrasound and tomosynthesis images and/or volumes.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method, comprising:
acquiring initial image data using a first imaging system;
identifying, using a processor, one or more regions of interest in at least one of the initial image data or in a first image generated from the initial image data;
automatically deriving, using the processor, one or more scan parameters for a subsequent image acquisition, wherein automatically deriving the one or more scan parameters comprises executing a change detection routine that detects changes in the one or more regions of interest relative to a previous examination and derives the one or more scan parameters based upon the detected changes; and
acquiring second image data using the scan parameters such that the second image data is limited to the one or more regions of interest.

2. The method of claim 1, wherein the regions of interest are identified automatically.

3. The method of claim 1, wherein the second image data is acquired automatically using the one or more scan parameters.

4. The method of claim 1, wherein the second image data is acquired using a different imaging modality than the initial image data.

5. The method of claim 1, wherein the regions of interest comprise at least one of anatomical structures or functional information of physiological processes.

6. The method of claim 1, wherein the regions of interest are identified by a computer aided diagnosis (CAD) algorithm, or by an operator reviewing possible regions of interest automatically selected by one or more routines.

7. The method of claim 1, comprising generating a second image based upon the second image data.

8. The method of claim 7, comprising combining the first image and the second image.

9. The method of claim 1, comprising generating a second image based on at least the first image data and the second image data.

10. An imaging system comprising:
a first imaging modality configured to acquire first image data from which a first image may be derived;
a processor configured to identify one or more regions of interest in the first image data or the first image, to detect changes in the one or more regions of interest relative to a previous examination, and to automatically derive one or more scan parameters based upon the detected changes; and
a second imaging modality configured to acquire second image data based upon the one or more scan parameters.

11. The imaging system of claim 10, wherein the first imaging modality is an X-ray tomosynthesis system and the second imaging modality is an ultrasound (US) system.

12. The imaging system of claim 10, comprising a control system coupled to the first and second imaging modalities, wherein the control system is configured to automatically acquire the first image data and the second image data.

13. A method comprising:
acquiring, using a X-ray based imaging modality, initial image data comprising X-ray projection data;
identifying, using a processor, regions of interest in at least one of the initial image data or in a first volumetric image reconstructed from the initial image data, wherein the one or more regions of interest comprise detected anatomical changes between the initial image data or the first volumetric image and an image acquired during a previous examination;
automatically deriving scan parameters, using the processor, for a subsequent image acquisition based upon the regions of interest, wherein the scan parameters are automatically derived based upon the detected anatomical changes; and
acquiring second image data using the scan parameters.

14. The method of claim 13, wherein acquiring the second image data using the scan parameters comprises automatically acquiring the second image data.

15. The method of claim 13, comprising generating a second image based on the second image data or based on a combination of the initial image data and the second image data.

16. The method of claim 13, comprising employing computer aided diagnosis (CAD) algorithms configured to identify the regions of interest.

17. A method, comprising:
acquiring, using a first imaging system, first image data from which a first image may be generated, wherein at least one of the first image data or the first image comprise one or more regions of interest;
acquiring, using a second imaging system, second image data based upon one or more scan parameters automatically derived based upon a change detection routine, executed by a processor, that detects changes in the one or more regions of interest relative to a previous examination and derives the one or more scan parameters for acquiring the second image data based upon the detected changes.

18. An imaging system comprising:
a processor configured to identify one or more regions of interest in first image data or a first image derived from the first image data, to detect changes in the one or more regions of interest relative to a previous examination, and to automatically derive one or more scan parameters based upon the detected changes; and
an imaging modality configured to acquire the first image data and to acquire second image data based upon the one or more scan parameters.

19. The imaging system of claim 18, comprising a control system coupled to the imaging modality, wherein the control system is configured to automatically acquire the first image data and the second image data.

20. The method of claim 1, wherein the one or more scan parameters comprise one or both of view angles or collimator settings of the subsequent image acquisition step.

21. The imaging system of claim 11, wherein the one or more regions of interest comprise the location of a skin-line of the patient and the one or more scan parameters based upon the location of the skin-line limit the acquisition of the second image data to a region bounded by the skin-line.

* * * * *